United States Patent [19]

Haring et al.

[11] Patent Number: 5,505,312
[45] Date of Patent: Apr. 9, 1996

[54] INSPECTION MACHINE FOR BOTTLES OR THE LIKE

[75] Inventors: Franz Haring, Neutraubling; Karl Griesbeck, Regensburg, both of Germany

[73] Assignee: Krones AG Hermann Kronseder Maschinenfabrik, Neutraubling, Germany

[21] Appl. No.: 275,023

[22] Filed: Jul. 13, 1994

[30] Foreign Application Priority Data

Jul. 16, 1993 [DE] Germany .............................. 9310623 U

[51] Int. Cl.⁶ ....................................................... B07C 5/00
[52] U.S. Cl. ........................... 209/524; 209/525; 209/526; 209/577; 209/580; 209/939
[58] Field of Search ...................................... 209/524, 525, 209/526, 523, 522, 577, 580, 939

[56] References Cited

U.S. PATENT DOCUMENTS

| | | |
|---|---|---|
| 4,680,463 | 7/1987 | Lutgendorf et al. . |
| 4,691,231 | 9/1987 | Fitzmorris et al. ................ 209/526 X |
| 4,915,237 | 4/1990 | Chang et al. ..................... 209/526 X |
| 5,059,031 | 10/1991 | Hamel et al. .................... 209/522 X |

FOREIGN PATENT DOCUMENTS 0124164  4/1984  European Pat. Off. .

4207835  9/1993  Germany ............................ 209/524

*Primary Examiner*—David H. Bollinger
*Attorney, Agent, or Firm*—Ryan, Maki & Hohenfeldt

[57] ABSTRACT

First, second and third linear conveyors are arranged in alignment with each other in the stated order. Bottles to be inspected are conveyed standing on their bottoms on the first linear conveyor through an inspection station followed by an ejector for those bottles which fail to match specified characteristics of an acceptable bottle model. The second conveyor has spaced apart parallel translating conveyor belts for frictionally gripping the bottles by their bodies between them to make their mouth ends and bottoms clear for inspection. The bottle discharge end region of the first conveyor and the bottle inlet end region overlap to achieve an overall shorter machine. The second conveyor has a bottle discharge region that overlaps the bottle inlet end region of the third conveyor to achieve a shorter machine. Bottles determined at the first conveyor inspection station to have one or more characteristics that do not match acceptable bottles are ejected and remaining bottles go on to be inspected for other characteristics at a station adjacent the second conveyor and those found to have one or more unacceptable characteristics differing from an acceptable bottle are ejected upon discharge from the second conveyor to the third conveyor.

16 Claims, 2 Drawing Sheets

INSPECTION MACHINE FOR BOTTLES OR THE LIKE

BACKGROUND OF THE INVENTION

The invention disclosed herein pertains to a machine for inspecting bottles and for separating from a conveyed stream of bottles those which are not acceptable because they are too short, too tall, contain foreign matter, are chipped, contain lye that is carried over from the washing machine, or that may have an undesired color, for example.

A straight in-line inspection machine for bottles is known from European patent EP 124 164 B1 and corresponding U.S. Pat. No. 4,680,463. In the known machine, there are first and second linear conveyors comprised of conveyor belts arranged in succession and alignment with each other. At the end of the first straight conveyor belt, there is a collection container into which can fall bottles that are tipped on their sides, glass fragments, and bottles which are too small to be grasped in a second conveyor between two parallel driven belts that are spaced apart sufficiently to grasp bottles having the proper size. In this design, especially when operated at high transport speeds, their is a risk that the undersized bottles will be slung from the end of the first linear conveyor over the collecting container and will fall on the floor of the inspection department, which is obviously undesirable. No provision is made in the known machine for ejecting oversized bottles. If an oversized bottle is present in the bottle stream and gets through the first conveyor, it will arrive on the second conveyor where it can strike and damage various bottle characteristic inspecting devices arranged along the second conveyor.

SUMMARY OF THE INVENTION

An achieved objective of the invention disclosed herein resides in providing a bottle and other glass container inspection machine that separates unacceptable bottles from a stream of bottles rapidly, efficiently and reliably.

According to the invention, the new inspection machine has first, second and third conveyors arranged in line with associated inspection devices for separating and rejecting bottles that have a great variety of undesirable characteristics from the majority of acceptable bottles, even separating and ejecting bottles on the first linear conveyor that have the wrong color, wrong shape or wrong height when compared with the majority of bottles in the stream that are destined to be filled with a beverage. Thus, avoidance of damage by bottles to the second and third consecutive linear conveyors and to inspection devices and instruments associated therewith is assured. The new inspection machine features overlapping consecutive conveyors so the length of the machine is shortened appreciably. It is a feature of the new machine to increase the spacing between the abutting bottles in the incoming stream for enhancing control of the bottles in the inspection zones and in the unacceptable bottle ejection zones. Spacing the bottles can be accomplished, for example, by passing them through a controlled starwheel or a worm conveyor or by having the infeed conveyor run at a slower speed than the first linear conveyor so they are accelerated on the first conveyor and are thereby have space between them separated.

A feature of the invention resides in arranging a bottle wall inspection device adjacent the first linear conveyor to perform multiple functions. Heretofore, wall inspection devices having an illuminating device on one side of the bottle stream and at least one electronic camera on the other side of the path of movement of the bottles are incapable of detecting bottles whose size deviates from the majority of bottles in the stream. According to the invention, the wall inspection device has the capability of detecting the presence of contaminants or foreign matter as well as the capability for detecting bottles that have the wrong shape to be considered candidates for being filled with a beverage. In the new machine, the ejector for bottles with nonconforming shapes or sizes is on the outlet side of the wall inspection arrangement. Thus, the inspection arrangement can be given responsibility for inspecting bottle walls and segregating unacceptable bottles. As a result, separate sensors for recognition of nonconforming bottles, that is, bottles that do not conform to the size and shape requirements of the majority of bottles in the stream are usually not required.

Various types of ejectors for rejected or unacceptable bottles can be used. A simple and reliable type is one having a head that can be projected or swung with an impulse to strike the unacceptable bottle for rejecting it. The head can be a sponge roller.

How the foregoing unique features of the new machine are achieved and implemented will be explained in conjunction with a more detailed description of a preferred embodiment of the invention which will now be set forth in reference to the accompanying drawings.

DESCRIPTION OF A PREFERRED EMBODIMENT

Figure 1:
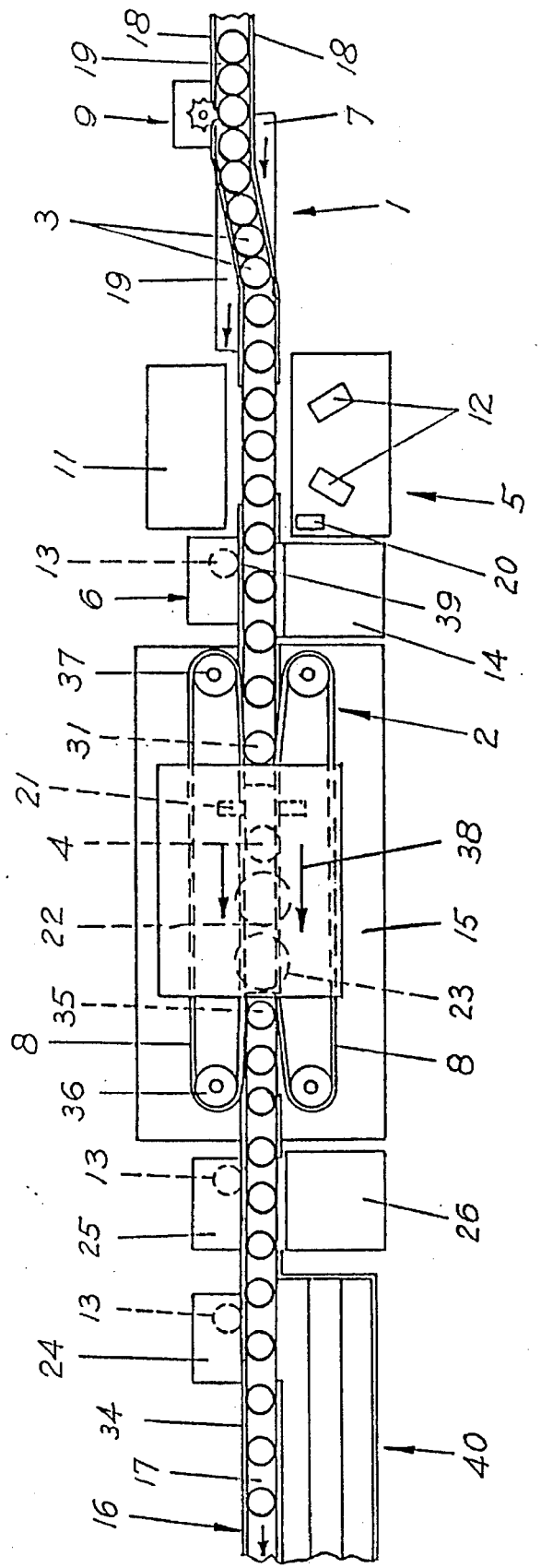
FIG. 1 is a top plan view of the new bottle inspection machine.
Figure 2:
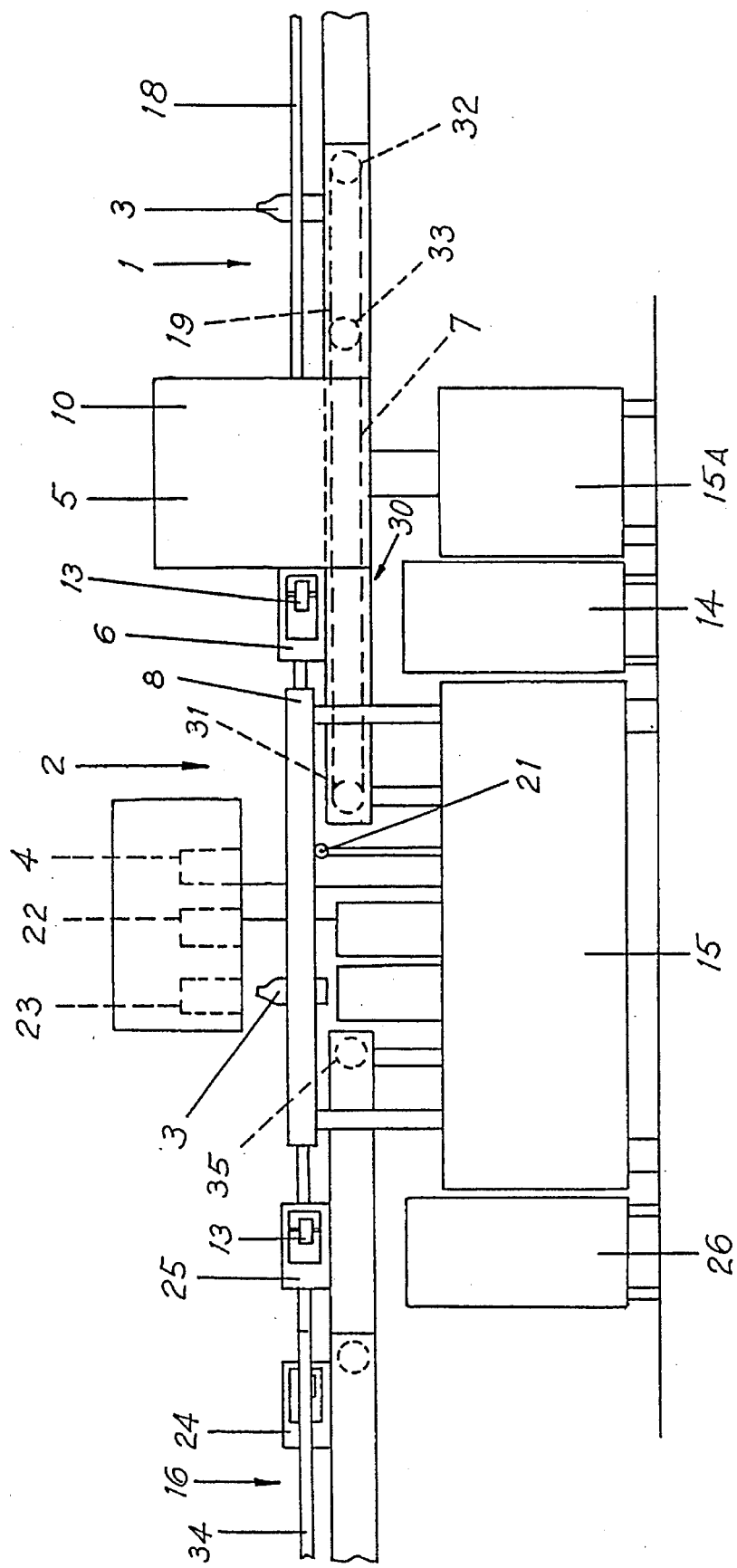
FIG. 2 is a side elevational view of the machine.

The inspection machine depicted in FIGS. 1 and 2 is designed for inspecting previously washed reusable glass beverage bottles and rejecting bottles that contain foreign bodies on their walls or bottoms or lye residues that are interior of the bottles and carried over from the bottle washing machine, for example. The new machine is designed to be installed in a bottle filling line between a bottle washing machine and a filling and capping machine. The washing and capping machines are not shown.

The machine has a housing comprised of two parts, 15 and 15A, in which various drive mechanisms and control devices, not visible, are accommodated. Above the height of the housing parts 15 and 15A a first linear conveyor 1, a second linear conveyor 2 and a third linear conveyor 16 are arranged. The three linear conveyors are aligned in such manner that bottles which are faultless and pass inspection in all stages of the inspection machine are conveyed through the machine in a continuous straight path.

First, linear conveyor 1 and third linear conveyor 16 each comprise endless conveyor belts 7 and 17, respectively, which run on wheels positioned within a framework 30. The profile of the framework is discernible in FIG. 2. The drive wheel for the first linear conveyor belt 7 is marked 31 and the idler wheel for the first conveyor belt is marked 32. A bottle infeed conveyor belt 19 at the far right regions of the drawings feeds incoming bottles 3 onto first linear conveyor belt 7. As one may perceive in FIG. 2, the idler wheel for infeed conveyor belt 19 is positioned axially of the idler wheel 32 for the first linear conveyor belt 7 but the wheels are independent of each other. The drive wheel for the infeed conveyor belt 19 is marked 33. The first and third linear conveyor belts 7 and 17, respectively, are disposed in the same horizontal plane. The infeed conveyor 19 and the bottle receiving end of the first linear conveyor belt 7 share common guiderails 18. The third linear conveyor belt 17 has guide rails 34 for the bottles. The guiderails are adjustable spatially to conform with the diameter of the bottles being inspected. The bottles 3 are transported in an upright attitude when they are on the first linear conveyor belt 7 and when they are on third linear conveyor belt 17 and they are supported from their bottoms on these conveyors. They are conveyed and transported in the second conveyor 2 while being gripped along their bodies to make their mouths and bottoms accessible for inspection as will be discussed momentarily.

As may be visualized in FIGS. 1 and 2, first linear conveyor belt 7 ends at drive wheel 31. Endless third linear conveyor belt 17 begins where it runs over a drive wheel 35. Thus, there is a gap equal to several bottle diameters between the end of first conveyor belt 7 and the beginning of third conveyor belt 17. This gap is bridged by a second linear conveyor that is designated generally by the reference numeral 2. Second linear conveyor 2 comprises endless driven belts 8 which face each other and run in the same direction as indicated by the arrows marked 38. The endless belts 8 run on driven rollers 36 and idler rollers 37 which rotate about vertical axes. Belts 8 have an elastic frictional coating on their outside faces and are spaced apart only sufficiently to allow them to grip bottles 3 in their body regions to transport the bottles while they hang vertically without bottom support through the gap between the first and third linear conveyor belts 7 and 17, respectively. From inspection of FIG. 2, one may see that the beginning of the belts 8 of the second linear conveyor 2 overlap the bottle discharge end 31 of the first conveyor 7 and the discharge end of the second linear conveyor 2, that is, the belts 8 thereof, overlap the beginning of the third linear conveyor belt 17. Conveyors 1, 2 and 16 are driven in synchronism, that is, at the same translational velocity.

The bottle 3 infeed conveyor belt 19 and the adjacent bottle guiderails 18 have been previously mentioned. The infeed conveyor belt 19 is driven translationally at a speed that is slightly slower than the first linear conveyor belt 7 so that the bottles 3, after having arrived on the faster first linear conveyor belt 7 are accelerated somewhat. This results in the bottles becoming uniformly spaced apart on the first linear conveyor 7. Before incoming bottles 3 begin their transfer from the infeed conveyor 19 to the inlet end of first linear conveyor belt 7 under the influence of the angularly directed guiderails 18, the bottles cause rotation of a freely rotatable starwheel 9 which can be blocked against rotation to stop infeed of bottles 3 to the inspection machine if the need to do so arises.

Before the bottles 3 are transferred from first linear conveyor 7 to second linear conveyor 2, the bottles pass through to a wall inspection station where they are inspected for defects, foreign substances and conformity with the shape and dimensions of an acceptable bottle type with a wall inspection device 5 comprised of a bottle illuminating device 11 on one side of first linear conveyor 7 for illuminating and projecting light through the bottles to allow electronic video cameras 12 to make two images of the passing bottles 3. An electronic evaluation device, not shown, analyzes the image data to determine first of all if the bottle being inspected at this station is one that conforms with the type of bottles that are to be filled. In other words, the inspection device determines if the bottle differs in contour or height from or any dimension acceptable bottles, for example. The bottle wall inspection station, the bottle walls are also inspected with the same devices preferably for foreign substances, which, if any are discovered, results in the bottle being identified for rejection. In some installations as in the one being described, a color sensor 20 is provided so that even if the bottles have the proper shape and height to be qualified for filling, they are identified for being ejected if their color is incorrect.

Bottles that fail to pass inspection at the bottle wall and bottom dimension inspection device 5 just described are ejected laterally from the stream of bottles by an ejector 6 that is positioned so ejection occurs before the bottles have a chance to enter the second linear conveyor 2 and do any damage there. To facilitate ejection, a gap 39 is formed in the guide rails adjacent a rejected bottle collecting container 14. Ejector device 6 has a sponge roll 13 arranged beside first linear conveyor belt 7. On arrival, adjacent the sponge roll of a bottle that has been identified for rejection, the sponge roll is impulsed by a pneumatic cylinder, not shown, into the path of the moving bottles 3 so the defective or unacceptable bottle is propelled into container 14.

Bottles 3 that pass wall inspection and size and shape inspection at inspection device 5 continue on first linear conveyor belt 7 until they become gripped frictionally between parallel laterally spaced apart friction belts 8 of second linear conveyor 2 wherein the bottles are conveyed upright with their bottoms and mouths clear of any obstruction.

In the second linear conveyor 2, the bottles are further inspected with a sensor 21 for detecting residual lye that may be carried over from a bottle washing machine, not shown. The bottoms of the respective bottles are also inspected by first and second inspection instruments 22 and 23 and there is a further inspection by a bottle mouth and thread inspection device 4.

After the various inspections of the bottles in second linear conveyor 2 are completed, the bottles are released from conveyor 2 onto the third linear conveyor belt 17 of conveyor system 16. At first, the bottles pass a rejection device 25 which is designed for exclusively ejecting bottles with defective mouth and/or threads into a dedicated container 26. Rejection device 25 is structurally the same as previously discussed ejection devices 6.

After acceptable bottles 3 pass thread and mouth defect rejector 25, the bottles pass a final good bottle ejector device 24 which is similar to the ejector 6. Device 24 ejects or transfers acceptable bottles laterally of a third linear conveyor belt 17 onto a collecting table 40 comprised of three parallel conveyor belts as shown.

What is claimed is:

1. A machine for inspecting bottles and separating unacceptable bottles from acceptable bottles comprising:

a first linear conveyor for conveying along a linear path a stream of bottles supported from their bottoms on the conveyor, a first inspection station including inspection apparatus adjacent said linear path operative to identify bottles that are unacceptable because they differ from acceptable bottles in size or shape, an ejector device downstream form said inspection station and operative to eject bottles laterally of the first linear conveyor that have been identified as unacceptable at said station, a second linear conveyor downstream of said ejector device in line with the first linear conveyor and arranged for receiving from said first linear conveyor bottles that have passed the ejector device, the second linear conveyor is operative to transport the bottles along a linear path while gripping the bottles in a manner for their bottoms and tops to be exposed for inspection.

2. A machine according to claim 1 wherein said first linear conveyor is comprised of at least one endless translationally driven belt on which the bottles are supported from their bottoms.

3. A machine according to claim 1 wherein said second linear conveyor is comprised of at least one closed loop belt that presses against the bottles to frictionally grip the bottles and convey them.

4. A machine according to claim 1 wherein said second linear conveyor is comprised of two translationally driven closed loop conveyor belts having corresponding portions running in the same direction in substantial parallelism and spaced apart from each other to define an elongated space having a bottle inlet end region and a downstream bottle discharge end region from which the bottles are released from the grip of the belts, said first linear conveyor, having a bottle inlet end region upstream from the inspection station and a bottle discharge end region downstream from said ejector device, the bottled discharge end region of the first linear conveyor arranged in overlapping relation to the bottle inlet region of the second conveyor.

5. A machine according to any one of claims 1, 2, 3 or 4 wherein said inspection station includes a light source on one side of said bottles conveyed in said linear path on said first linear conveyor and at least one electronic camera on the opposite side of said linear path, the camera making at least one image of the wall of each passing bottle illuminated by the light source for comparing with an image of a bottle having an acceptable wall, lack of a comparison causing said ejector to respond by ejecting the bottle.

6. A machine according to any one of claims 1, 2, 3 or 4 adapted for inspecting the walls of the bottles wherein the inspection station includes a light source on one side of said linear path in which the bottles are conveyed for illuminating said bottles and at least one video camera on the opposite side of said linear path, the camera making at least one image of the wall of a passing bottle for comparison with an image of a bottle having an acceptable wall, lack of a comparison causing said ejector to respond by ejecting the bottle.

7. A machine according to any one of claims 1, 2, 3 or 4 including a color responsive detector in the inspection station to which said bottles are exposed, said ejector responding to detection of a bottle having unacceptable color by ejecting the bottle.

8. A machine according to claim 1 wherein said inspection apparatus at said first inspection station comprises a light source on one side of said bottles conveyed in said linear path on said first conveyor for illuminating the bottles as they pass, at least one electronic camera on the opposite side of the linear path, the camera making at least one image of each bottle for comparison of the size and shape of the bottle and the condition of the wall of the bottle with an image of an acceptable bottle that has an acceptable size and shape and a wall that is free of foreign matter, said ejector responding to the image of the bottles under inspection differing from an acceptable bottle by ejecting the differing bottle.

9. A machine according to any one of claims 1, 3 or 4 including:

at least one device proximate to the linear path of the bottles in said second conveyor for inspecting the bottom of bottles on the conveyor.

10. A machine according to any one of claims 1, 3 or 4 including:

a device proximate the linear path of the bottles in said second conveyor for inspecting the mouths of bottles on the conveyor.

11. A machine according to any one of claims 1, 3 or 4 including:

a device proximate the linear path of the bottles in said second conveyor for inspecting the threads of bottles on the conveyor.

12. A machine according to any one of claims 1, 3 or 4 including:

a device proximate the linear path of the bottles in said second conveyor for inspecting the bottles for lye in the interior of the bottles.

13. A machine according to claim 4 including an unacceptable bottle ejector downstream from said bottle discharge end of the second conveyor.

14. A machine according to any one of claims 1, 3 or 4 including:

a third linear conveyor arranged in alignment with said second linear conveyor for conveying bottles discharged from said second linear conveyor.

15. A machine according to any one of claims 1, 3 or 4 including a third linear conveyor for conveying bottles discharged from said second linear conveyor, the third conveyor arranged in alignment with the second conveyor, said third conveyor having a bottle inlet end region and said second linear conveyor overlapping the inlet end region.

16. A machine according to claim 1 wherein:

said first linear conveyor has a bottle inlet end region upstream from said inspection station, a bottle infeed conveyor laterally adjacent said inlet end region of the first linear conveyor and operative to convey bottles in the direction of translation of the first linear conveyor, guide means extending over said infeed conveyor and said inlet end region of the first linear conveyor at an angle relative to the direction of movement of the first linear conveyor and the infeed conveyor for deflecting bottles conveyed on the infeed conveyor onto the first linear conveyor, said first linear conveyor being driven translationally at a speed greater than the speed of the infeed conveyor to cause a space to develop between successive bottles as they arrive on the inlet end region of the first conveyor.

* * * * *